United States Patent [19]

Wess et al.

[11] Patent Number: 4,855,323

[45] Date of Patent: Aug. 8, 1989

[54] LEUKOTRIENE ANTAGONISTS, A PROCESS FOR THE PREPARATION THEREOF, AND THE USE THEREOF FOR THE TREATMENT OF DISEASES

[75] Inventors: Günther Wess, Erlensee; Wilhelm Bartmann, Bad Soden am Taunus; Gerhard Beck, Frankfurt am Main; Hiristo Anagnostopulos, Taunusstein, all of Fed. Rep. of Germany

[73] Assignee: Hoechst Aktiengesellschaft, Frankfurt am Main, Fed. Rep. of Germany

[21] Appl. No.: 223,129

[22] Filed: Jul. 22, 1988

[30] Foreign Application Priority Data

Jul. 25, 1987 [DE] Fed. Rep. of Germany ....... 3724669

[51] Int. Cl.$^4$ ................. A61K 31/215; C07C 149/273
[52] U.S. Cl. .................... 514/550; 514/532; 514/570; 514/571; 514/618; 560/11; 560/15; 560/17; 560/60; 562/426; 562/429; 562/470; 564/161; 564/162; 564/169; 564/170
[58] Field of Search .................. 560/11, 15, 60, 17; 562/426, 429, 470; 514/532, 570, 571, 550, 618; 564/161, 162, 169, 170

[56] References Cited

U.S. PATENT DOCUMENTS

| | | | |
|---|---|---|---|
| 3,867,434 | 2/1975 | Diamond | 562/426 |
| 3,894,080 | 7/1975 | Diamond et al. | 564/162 |
| 3,993,683 | 11/1976 | Nickl et al. | 564/162 |
| 4,785,004 | 11/1988 | Von Sprecher et al. | 574/532 |

FOREIGN PATENT DOCUMENTS 2101594 1/1983 United Kingdom ............... 560/17

OTHER PUBLICATIONS

Musser et al., Agents and Actions, vol. 18, pp. 332–341 (1986).
Gleason et al., Journal of Medicinal Chemistry, vol. 30, No. 6, pp. 959–961 (1987).

Primary Examiner—James H. Reamer
Assistant Examiner—Julie K. Parker
Attorney, Agent, or Firm—Finnegan, Henderson, Farabow, Garrett & Dunner

[57] ABSTRACT

Leukotriene antagonists, a process for the preparation thereof, and the use thereof for the treatment of diseases

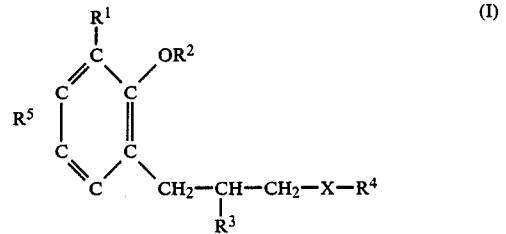

in which $R^1$, $R^2$, $R^3$, $R^4$, $R^5$ and X have the indicated meanings, a process for the preparation of these compounds, the use thereof as pharmaceuticals, and pharmaceutical products based on these compounds, are described.

14 Claims, No Drawings

LEUKOTRIENE ANTAGONISTS, A PROCESS FOR THE PREPARATION THEREOF, AND THE USE THEREOF FOR THE TREATMENT OF DISEASES

The invention relates to new chemical compounds which, as such or in the form of their pharmacologically tolerated salts, have a leukotriene-antagonsitic action, to process for the preparation of these compounds, to pharmaceutical agents which contain the active compounds according to the invention, and to the use thereof, especially for the treatment of diseases which are associated with an elevated leukotriene level, for example asthma.

In response to various stimuli, for example those elicited by allergens, basophilic cells and mast cells release a mediator which is called SRS-A (slow reacting substance of anaphylaxis) and which shows both in animal experiments and in humans an extremely strong bronchoconstricting effect and presumably plays an important part in asthmatic disorders. It was shown some years ago that SRS-A is a mixture of the leukotrienes $LTC_4$, $LTD_4$ and $LTE_4$, which are produced from arachidonic acid via what is called the 5-lipoxygenase pathway. It is assumed that the leukotrienes also play an important part in other part in allergic and inflammatory disorders, such as allergic skin reactions, psoriasis, ulcerative colitis and rheumatoid arthritis, as well as in shock.

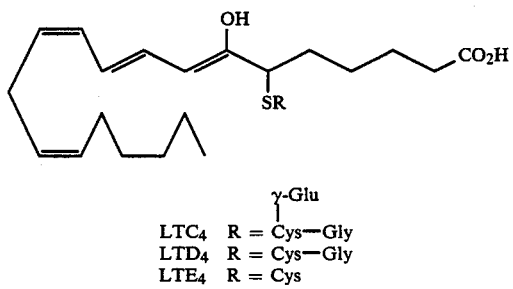

The biological effect of the leukotrienes is mediated by specific receptors on the target cells (smooth muscle cells, macrophages etc.). This is why compounds which are able to block these receptors (i.e. receptor antagonists) ought to be suitable for the treatment of the abovementioned diseases.

It has already been described how certain alterations in the basic structure of the leukotrienes (saturation of some of the double bonds, incorporation of a benzene ring into the chain, shortening, modification or complete omission of the peptide side-chain or of the terminal carboxyl group) may result in partial agonists or antagosists (for a review, see John H. Musse et al., Agents and Actions 18, 332-41 (1986), and John G. Gleason et al., J. Med. Chem. 30 (6), 959-61, (1987)). However, many of the leukotriene analogs described hitherto still have agonsitic properties or, apart from a few exceptions, have insufficient in vivo activity or no oral activity.

We have now found, surprisingly, that the basic structure of the leukotrienes can be even more extensively modified than hitherto described without losing the desired antagonistic action.

Hence the invention relates to new compounds of the general formula I:

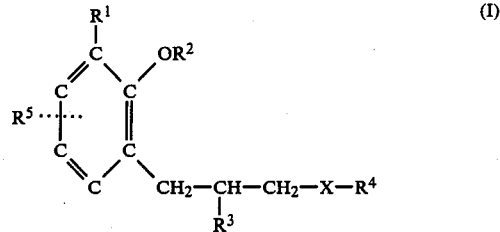

where the radicals have the following meaning:

X is O, S, SO, or $SO_2$;

$R^1$ is H, $C_1-C_{12}$-alkyl, $C_2-C_{12}$-alkenyl or $C_2-C_{12}$-alkynyl (straight-chain or branched), $C_3-C_8$-cycloalkyl, $C_3-C_8$-cycloalkenyl, halogen, phenoxy, $CF_3$, $NO_2$, OH, $OR^6$, COOH, $COOR^6$, CHO or $COR^7$;

$R^2$ is H, $C_1-C_{12}$-alkyl, $C_2-C_{12}$-alkenyl or $C_2-C_{12}$-alkynyl (straight-chain or branched), $C_3-C_8$-cycloalkyl, $C_3-C_8$-cycloalkenyl, phenyl-$C_1-C_{10}$-alkyl, phenoxy-$C_1-C_{10}$-alkyl, phenyl-$C_2-C_{10}$-alkenyl or phenyl-$C_2-C_{10}$-alkynyl, it being possible for the phenyl rings also to be substituted by 1-3 $C_1-C_4$-alkyl, $C_2-C_4$-alkenyl, $C_1-C_4$-alkoxy, $C_1-C_4$-alkanoyl, $C_1-C_4$-alkoxycarbonyl, hydroxyl or halogen radicals, or $R^2$ is pyridylmethyl or thienylmethyl;

$R^3$ is OH, $OR^6$ or $OCOR^7$;

$R^4$ is $C_1-C_4$-alkyl, $C_2-C_4$-hydroxyalkyl, $C_3-C_4$-dihydroxyalkyl, $C_1-C_4$-alkoxy-$C_1-C_4$-alkyl, $C_1-C_4$-alkanoyloxy-$C_1-C_4$-alkyl, phenyl or phenyl-$C_1-C_4$-alkyl, it being possible for the phenyl rings to be substituted once or twice by HO, halogen, $C_1-C_4$-alkoxy or $C_1-C_4$-alkylthio, or $R^4$ is a group of the general formula $(CH_2)_nCOR^8$ or $(CH_2)_nR^9$;

$R^5$ is H, halogen, $CF_3$, OH, $C_1-C_4$-alkyl or $C_1-C_4$-alkoxy;

$R^6$ is $C_1-C_4$-alkyl, allyl or benzyl; $R^7$ is $C_1-C_4$-alkyl or phenyl;

$R^8$ is OH, $C_1-C_4$-alkoxy, $CH_2OH$, $OCH_2CO_2H$, $OCH_2CO_2R^7$, $OCH_2Ph$, NHOH, $NH_2$, $NHR^7$, $NR^7_2$, piperidino, pyrrolidino, morpholino or phenoxy, it being possible for the phenoxy radical also to be substituted by carboxyl, $C_1-C_4$-alkoxycarbonyl, OH or $OCH_3$;

$R^9$ is tetrazol-5-yl or 2-oxo-1,3-dioxolan-4-yl;

n is 0, 1, 2 or 3; as well as to physiologically tolerated salts of those compounds of the general formula I in which one of the radicals contains a carboxyl group (COOH).

Preferred compounds of the general formula I are those in which the radicals have the following meaning:

X is O, S, SO or $SO_2$;

$R^1$ is H, $C_1-C_4$-alkyl, $C_3-C_8$-cycloalkyl or $C_3-C_8$-cycloalkenyl;

$R^2$ is H, $C_1-C_{10}$-alkyl (straight-chain or branched), $C_3-C_8$-cycloalkyl, phenyl-$C_1-C_{10}$-alkyl or phenoxy-$C_1-C_{10}$-alkyl, it being possible for the phenyl rings also to be substituted by 1-3 $C_1-C_4$-alkyl, $C_2-C_4$-alkenyl, $C_1-C_4$-alkoxy, $C_1-C_4$-alkanoyl, $C_1-C_4$-alkoxycarbonyl, hydroxyl or halogen radicals, or $R^2$ is pyridylmethyl or thienylmethyl;

$R^3$ is OH;

$R^4$ is $C_1-C_4$-alkyl, $C_2-C_4$-hydroxyalkyl, $C_3-C_4$-dihydroxyalkyl, $C_1-C_4$-alkoxy-$C_1-C_4$-alkyl, $C_1-C_4$-alkanoyloxy-$C_1-C_4$-alkyl, phenyl or phenyl-$C_1-C_4$-alkyl, it being possible for the phenyl rings to be substituted once or twice by HO, halogen, $C_1-C_4$-alkoxy or $C_1$–$C_4$-alkylthio, or $R^4$ is a group of the general formula $(CH_2)_nCOR^8$ or $(CH_2)_nR^9$;

$R^5$ is H or halogen;

$R^7$ is $C_1$–$C_4$-alkyl;

$R^8$ is OH, $C_1$–$C_4$-alkoxy, $CH_2OH$, $OCH_2CO_2H$, $OCH_2CO_2R^7$, $OCH_2Ph$, NHOH, $NH_2$, $NHR^7$, $NR^7{}_2$, piperidino, pyrrolidino, morpholino, or phenoxy, it being possible for the phenoxy radical also to be substituted by carboxyl, $C_1$–$C_4$-alkoxylcarbonyl, OH or $OCH_3$;

$R^9$ is tetrazol-5-yl;

n is 1, 2 or 3.

Particularly preferred compounds of the general formula I are those in which the radicals have the following meaning:

X is S;

$R^1$ is H, $CH_3$ or cyclopentyl;

$R^2$ is H, benzyl, it being possible for the benzyl radical also to be substituted once or twice on the phenyl ring by methoxy or chlorine, is phenoxy-$C_2$–$C_4$-alkyl, it being possible for the phenyl ring also to be substituted by 1-3 $C_1$–$C_4$-alkyl, $C_1$–$C_4$-alkanoyl or hydroxy groups, or is pyridylmethyl or thienylmethyl;

$R^3$ is OH;

$R^4$ is $C_1$–$C_4$-alkyl, $C_2$–$C_4$-hydroxyalkyl, $C_3$–$C_4$-dihydroxyalkyl, $C_1$–$C_4$-alkoxy-$C_1$–$C_4$-alkyl, $C_1$–$C_4$-alkanoyloxy-$C_1$–$C_4$-alkyl, phenyl or benzyl, it being possible for the phenyl rings to be substituted once or twice by HO, methoxy or methylthio, or $R^4$ is a group of the general formula $(CH_2)_nCOR^8$ or $(CH_2)_nR^9$, $R^5$ is H or chlorine;

$R^7$ is $C_1$–$C_4$-alkyl;

$R^8$ is OH, $C_1$–$C_4$-alkoxy, $CH_2OH$, $OCH_2CO_2H$, $OCH_2CO_2R^7$, $OCH_2Ph$, NHOH, $NH_2$, piperidino, pyrrolidino, morpholino, or phenoxy, it being possible for the phenoxy radical also to be substituted by carboxyl, $C_1$–$C_4$alkoxycarbonyl, OH or $OCH_3$;

$R^9$ is tetrazol-5-yl;

n is 1, 2 or 3.

The following compounds are especially preferred:

Methyl (6RS)-7-(2-benzyloxyphenyl)-6-hydroxy-4-thiaheptanoate

Methyl (6RS)-7-(2-benzyloxy-3-cyclopentylphenyl)-6-hydroxy-4-thiaheptanoate

Methyl (6RS)-7-(2-benzyloxy-3-methylphenyl)-6-hydroxy-4-thiaheptanoate

Methyl (6RS)-7-(2-benzyloxy-3,5-dimethylphenyl)-6-hydroxy-4-thiaheptanoate (6RS)-7-(2-Benzyloxy-3-cyclopentylphenyl)-6-hydroxy-4-thiaheptanoic acid Methyl (6RS)-7-(2-benzyloxy-5-chlorophenyl)-6-hydroxy-4-thiaheptanoate (5RS)-6-(2-Benzyloxy-3-cyclopentylphenyl)-3-thiahexane-1,5-diol As is evident from the general formula I, the compounds according to the invention contain an asymmertric carbon atom (trhe one on which the radical $R^3$ is located). Hence the invention relates not only to the racemates of the compounds according to the invention but also to the enantiomers thereof.

The invention also relates to a process for the preparation of compounds of the formula I according to the invention.

The process for the preparation of the compounds of the formula I comprises A) reacting a compound of the general formula II

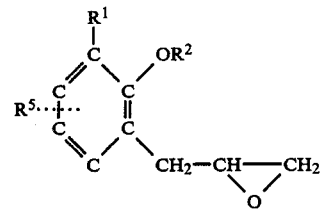

in which the radicals $R^1$, $R^2$ and $R^5$ have the meaning mentioned for formula I, with a compound of the general formula $R^4XH$, where $R^4$ has the meaning mentioned for formula I, and X is O or S, to give a compound of the formula I in which $R^1$, $R^2$, $R^4$ and $R^5$ have the indicated meaning, $R^3$ is the hydroxyl group, and X denotes sulfur or oxygen, or B) reacting a compound of the general formula III

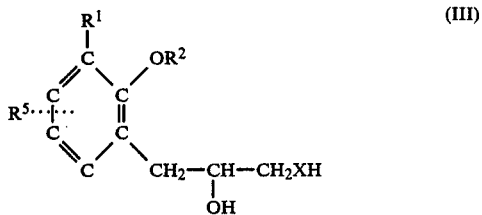

in which the radicals $R^1$, $R^2$ and $R^5$ have the meaning mentioned for formula I, and X denotes O or S, with a compound of the general formula $R^4Y$, where $R^4$ has the meaning mentioned for formula I, and Y is a leaving group such as, for example, Cl, Br, I, $OSO_2CH_3$, $OSO_2Ph$, $OSO_2Tol$, $OSO_2CF_3$ or $OSO_2R^4$, to give a compound of the formula I in which $R^1$, $R^2$, $R^4$ and $R^5$ have the indicated meaning, $R^3$ is the hydroxyl group and X denotes sulfur or oxygen, and, where appropriate, transforming a resulting compound by conversion into other compounds of the formula I.

The compounds of the formula I, according to the invention, in which the radical $R^3$ is OH can be prepared by the routes summarized in the scheme.

Process A comprises reacting an epoxide of the general formula II in which $R^1$, $R^2$ and $R^5$ have the same meaning as in formula I with an alcohol of the general formula $R^4OH$, or a mercaptan of the general formula $R^4SH$, where $R^4$ has the meaning mentioned for formula I. The reaction is advantageously carried out in an inert organic solvent such as toluene, tetrahydrofuran, diethyl ether, tert.-butyl methyl ether, dimethylformamide or dimethyl sulfoxide Scheme

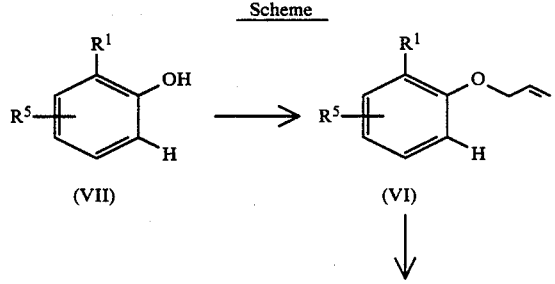

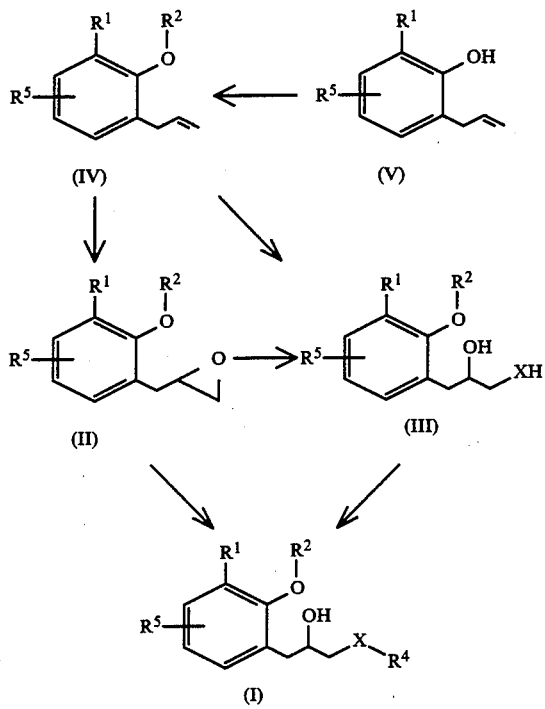

—lower alcohols such as methanol, ethanol, isopropanol or tert.butanol are also suitable for the mercaptans—in the presence of a base. Suitable bases in the case of the alcohols $R^4OH$ are particularly strong bases such as potassium tert.butylate, sodium hydride or lithium alkyls (preferably n-butyllithium); sodium hydride is preferred. In the case of the mercaptans $R^4SH$ it is also possible to use weaker bases such as tert.amines, especially trialkylamines, preferably triethylamine, diisopropylethylamine or 1,4-diazabicyclo[2.2.2]octane (DABCO), or tertiary amidines, especially bicyclic amidines, preferably 1,5-diazabicyclo[4.3.0]non-5-ene (DBN) or 1,8-diazabicyclo[5.4.0]undec-7-ene (DBU). When the reaction with the mercaptans $R^4SH$ is carried out in a lower alcohol, it is also possible advantageously to use the corresponding sodium or potassium alcoholates as base.

The reaction is carried out at temperatures from −20° C. to the boiling point of the solvent used. A temperature range from 0° to 120° C. is preferred, especially from 20° to 80° C.

The preferred embodiment of process A for the preparation of compounds of the formula I, according to the invention, in which $R^3$ is OH and X is O comprises reaction of a compound of the formula II with an alcohol $R^4OH$ in the presence of sodium hydrides in dimethylformamide or tetrahydrofuran at temperatures from 20° to 60° C. This reaction is advantageously carried out with exclusion of moisture or under a protective gas (nitrogen or argon).

The preferred embodiment of process A for the preparation of compounds of the formula I, according to the invention, in which $R^3$ is OH and X is S comprises reaction of a compound of the formula II with a mercaptan $R^4SH$ in the presence of triethylamine or DBU in tetrahydrofuran or methanol (if the group $R^4$ contains an ester, it is advantageous to use the alcohol contained in this ester) at temperatures from 20° to 60° C. This reaction is advantageously carried out under a protective gas (nitrogen or argon).

The starting materials of the general formula II required for process A can be obtained by standard epoxidation processes known to the expert from the corresponding olefins of the general formula IV (see Houben-Weyl,) Methoden der organischen Chemie (Methods of Organic Chemistry), volume VI/3, pages 385 et seq.). The latter can in turn easily be prepared from the 2-allylphenols of the general formula V by alkylation with halides or sulfonates of the type $R^2Y$ using standard processes (see Houben-Weyl, volume VI/3, pages 49 et seq.). 2-Allyphenols of the general formula V can be obtained by Claisen rearrangement of allyl phenyl ethers of the general formula VI (see Houben-Weyl, volume VI/1c, pages 502 et seq.). The latter can, where not commerically available, in turn be obtained very straightforwardly by alkylation of phenols of the general formula VII with allyl chloride. A large number of standard processes is available for the preparation of those phenols VII which cannot be brought (see Houben Weyl, volume VI/1c).

Process B comprises reacting a compound of the general formula III in which $R^1$, $R^2$ and $R^5$ have the same meaning as in formula I, and X is O or S, with a compound of the general formula $R^4Y$, where $R^4$ has the meaning mentioned for formula I, and Y is a leaving group such as Cl, Br, I or $OSO_2Z$ (Z=$CH_3$, Ph, tolyl, $CF_3$ or $OR^4$). The reaction is advantageously carried out in an inert organic solvent such as toluene, tetrahydrofuran, diethyl ether, tert.butyl methyl ether, dimethylformamide or dimethylsulfoxide—lower alcohols such as methanol, ethanol, isopropanol or tert.butanol are also suitable for the compounds of the general formula III in which X is S—in the presence of a base. Suitable bases in the case of the compounds of the general formula III in which X is O are particularly strong bases such as potassium tert.butylate, ssodium hydride or lithium alkyls (preferably n-butyllithium); sodium hydride is preferred. It is also possible in the case of the compounds of the general formula III in which X is S to use weaker bases such as tert.amines, especially trialkylamines, perferably triethylamine, diisospropylethylamine or 1,4-diazabicyclo[2.2.2]-octane (DABCO), or tertiary amidines, especially bicyclic amidines), preferably 1,5-diazabicyclo[4.3.0]non-5-ene (DBN) or 1,8-diazabicyclo[5.4.0]undec-7-ene (DBU). When the reaction with the compounds of the general formula III in which X is S is carried out in a lower alcohol, it is also possible advantageously to use the corresponding sodium or potassium alcoholates as base.

The reaction is carried out at temperatures from −20° C. to the boiling point of the solvent used. A temperature range from 0° to 120° C. is preferred, especially from 20° to 80° C.

Process B is less suitable for preparing those compounds of the formula I in which the radical $R^4$ is phenyl.

The preferred embodiment of process B for preparing compounds of the formula I, according to the invention, in which $R^3$ is OH and X is O comprises reaction of a compound of the general formula III in which X is O with a compound $R^4Y$ in the presence of sodium hydride in dimethylformamide or tetrahydrofuran at temperatures from 20° to 60° C. This reaction is advantageously carried out with exclusive of moisture or under a protective gas (nitrogen or argon).

The preferred embodiment of process B for preparing compounds of the formula I, according to the invention, in which $R^3$ is OH and X is S comprises reaction of a compound of the formula III in which X is S with a compound $R^4Y$ in the presence of triethylamine, sodium methanolate or DBU in tetrahydrofuran or methanol (if the group $R^4$ contains an ester, it is advantageous to use the alcohol contained in this ester) at temperatures from 20° to 60° C. This reaction is advantageously carried out under a protective gas (nitrogen or argon).

The starting compounds of the general formula III required for process B can be prepared from the epoxides of the general formula II by processes which are familiar to the expert (Houben-Weyl, volume VI/3, pages 454 et seq. (for X=O) and pages 461 et seq. (for X=S)). Particularly suitable for the preparation of the compound of the general formula III in which X is S is known opening of epoxides with thioacetic acid, followed by alkaline hydrolysis of the resulting thioester. Compounds of the general formula III in which X is O can also be obtained from the olefins of the general formula IV by hydroxylation using standard processes (osmium tetroxide, formic acid/$H_2O_2$ etc.).

A number of compounds of the general formula I according to the invention can also be obtained by transformation of other compounds of the formula I according to the invention.

Compounds of the general formula I in which $R^3$ is $OR^6$ can be obtained from compounds of the general formula I in which $R^3$ is OH by reaction with a compound of the general formula $R^6Y$, where $R^6$ has the meaning mentioned for formula I, and Y is a leaving group such as Cl, Br, I or $OSO_2Z$ (Z=$CH_3$, Ph, tolyl, $CF_3$ or $OR^6$). The reaction is advantageously carried out in an inert organic solvent such as toluene, tetrahydrofuran, diethyl ether, tert. butyl methyl ether, dimethylformamide or dimethyl sulfoxide in the presence of a base. Suitable bases are particularly strong bases such as potassium tert.butylate, sodium hydride or lithium alkyls (preferably n-butyllithium); sodium hydride is preferred.

The reaction is carried out at temperatures from −20° C. to the boiling point of the solvent used. A temperature range from 0° to 120° C. is preferred, especially from 20° to 80° C.

The preferred embodiment of the process for the preparation of compounds of the formula I, according to the invention, in which $R^3$ is $OR^6$ comprises reaction of a compound of the general formula I in which $R^3$ is OH with a compound $R^6Y$ in the presence of sodium hydride in dimethylformamide or tetrahydrofuran at temperatures from 20° to 60° C. This reaction is advantageously carried out with exclusion of moisture or under a protective gas (nitrogen or argon).

Compounds of the general formula I in which $R^3$ is $OCOR^7$ can be obtained from compounds of the general formula I in which $R^3$ is OH by acylation with a compound of the general formula $R^7COCl$, $R^7COBr$ or $(R^7CO)_2O$, where $R^7$ has the meaning mentioned for formula I. The reaction is advantageously carried out in pyridine or in a mixture of pyridine with an inert organic solvent such as toluene, tetrahydrofuran, diethyl ether, methylene chloride or tert.butyl methyl ether. The reaction rate can be increased by addition of 5–100 mol-% of an acylation catalyst such as 4-dimethylaminopyridine, 4-pyrrolidinopyridine or 4-piperidinopyridine.

The reaction is carried out at temperatures from −20° C. to the boiling point of the solvent used. A temperature range from −20° to 50° C. is preferred, especially from 0° to 25° C.

The preferred embodiment of the process for the preparation of compounds of the formula I, according to the invention, in which $R^3$ is $OCOR^7$ comprises reaction of a compound of the general formula I in which $R^3$ is OH with an organic acid chloride $R^7COCl$ or anydride $(R^7CO)_2O$ in pyridine in the presence of 10–20 mol-% of 4-dimethylaminopyridine at temperatures from 0° to 20° C. This reaction is advantageously carried out with exclusion of moisture of under a protective gas (nitrogen or argon).

Compounds of the general formula I in which $R^4$ is $C_1$–$C_4$-alkanoyloxy-$C_2$–$C_4$-alkyl can be obtained from compounds of the general formula I in which $R^4$ is $C_2$–$C_4$-hydroxyalkyl by acylation with a $C_1$–$C_4$-carboxylic acid chloride or anhydride. The reaction is advantageously carried out in pyridine or in a mixture of pyridine with an inert organic solvent such as toluene, tetrahydrofuran,. diethyl ether, methylene chloride or tert.butyl methyl ether. The reaction rate can be increased by addition of 5–100 mol-% of an acylation catalyst such as 4-dimethylaminopyridine, 4-pyrrolidinopyridine or 4-piperidinopyridine.

The reaction is carried out at temperatures from −20° C. to the boiling point of the solvent used. A temperature range from −20° to 50° C. is preferred, especially from 0° to 25° C.

Compounds of the general formula I in which $R^4$ is $C_1$–$C_4$-alkoxy-$C_2$–$C_4$-alkyl can be obtained from compounds of the general formula I in which $R^4$ is $C_2$–$C_4$-hydroxyalkyl by alkylation with a $C_1$–$C_4$-alkyl halide, sulfonate or sulfate. The reaction is advantageously carried out in an inert organic solvent such as toluene, tetrahydrofuran, diethyl ether, tert.butyl methyl ether, dimethylformamide or dimethyl sulfoxide in the presence of a base. Suitable bases are particulary strong bases as potassium tert.butylate, sodium hydride or lithyium alkyls (preferably n-butyllithium), and sodium hydride is preferred.

The reaction is carried out at temperatures from −20° C. to the boiling point of the solvent used. A temperature range from 0° to 120° C. is preferred, especially from 20° to 80° C.

Compounds of the general formula I in which $R^4$ is $(CH_2)_n COOH$ and n is 1–3, can be obtained from compounds of the general formula I in which $R^4$ is $C_2$–$C_4$-hydroxyalkyl by oxidation with suitable oxidizing agents known to the expert. The choice of the oxidizing agent is determined by the nature of the other radicals in the molecule. Suitable examples are pyridinium dichromate in dimethylformamide, chromic/sulfuric acid in water, acetic acid or acetone (Jones oxidation) or reuthenium trichloride (catalytic amounts) in the presence of cooxidants such as $K_2S_2O_8$ or $NaIO_4$ in water/$CCl_4$/acetonitrile or water/$CH_2Cl_2$ systems.

The reaction is carried out at temperatures from −20° C. to the boiling point of the solvent used. A temperature range from 0° to 50° C. is preferred, especially from 0° C. to 30° C.

Compounds of the general formula I in which $R^4$ is $C_2$–$C_4$-hydroxyalkyl can be obtained from compounds of the general formula I in which $R^4$ is $(CH_2)_n COR^8$, n is 1–3 and $R^8$ is OH, $C_1$–$C_4$-alkoxy, phenoxy or benzyloxy by reduction with suitable reducing agents known to the expert. Particularly suitable are complex hydrides such as borane (preferably as a complex with dimethyl sulfide or tetrahydrofuran), sodium borohydride, lithium borohydride, lithium aluminum hydride, diisobutylaluminum hydride or aluminum hydride. The reaction is advantageously carried out in an inert organic solvent such as toluene, tetrahydrofuran, diethyl ether, tert.-butyl methyl ether or methylene chloride.

The reaction is carried out at temperatures from −20° C. to the boiling point of the solvent used. A temperature range from 0° to 100° C. is preferred, especially from 10° to 70° C.

Compounds of the general formula I in which $R^4$ is $C_2$-$C_4$-hydroxyalkyl can be obtained from compounds of the general formula I in which $R^4$ is $C_1$-$C_4$-alkanoyloxy-$C_2$-$C_4$-alkyl by hydrolysis or aminolysis. Suitable reagents are bases such as sodium hydroxide, potassium hydroxide, barium hydroxide, calcium hydroxide, potassium carbonate, sodium carbonate, sodium or potassium alcoholates, ammonia, $C_1$-$C_4$-alkylamines, ethylenediamine or 2-aminoethanol in lower alcohols or alcohol/water mixtures as solvents. It is also possible to use no solvent in the case of the amines.

The reaction is carried out at temperatures from −20° C. to the boiling point of the solvent used. A temperature range from 0° to 100° C. is preferred, especially from 20° to 70° C.

Compounds of the general formula I in which $R^4$ is $(CH_2)_nCOR^8$ and $R^8$ is OH can be obtained from compounds of the general formula I in which $R^4$ is $(CH_2)_nCOR^8$ and $R^8$ is $C_1$-$C_4$-alkoxy, phenoxy or benzyloxy by hydrolysis by standard processes known to the expert. Particularly suitable is alkaline hydrolysis with bases such as sodium hydroxide, potassium hydroxide, barium hydroxide, calcium hydroxide, potassium carbonate or sodium carbonate in a lower alcohol or alcohol/water mixtures.

The reaction is carried out at temperatures from 0° C. to the boiling point of the solvent used. A temperature range from 20° to 100° C. is preferred, especially from 20° to 70° C.

Compounds of the general formula I in which $R^4$ is $(CH_2)_nCOR^8$ and $R^8$ is $C_1$-$C_4$-alkoxy or benzyloxy can be obtained from compounds of the general formula I in which $R^4$ is $(CH_2)_nCOR^8$ and $R^8$ is OH by esterification by standard processes known to the expert. Particularly suitable is alkylating esterification by reaction with a $C_1$-$C_4$-alkyl halide, sulfonate or sulfate or benzyl chloride or bromide in the presence of a base such as potassium carbonate, potassium fluoride, 1,4-diazabicyclo[2.2.2]octane (DABCO), 1,5-diazabicyclo[4.3.0]non-5-ene (DBN) or 1,8-diaezabicyclo[5.4.0]undec-7-ene (DBU) in a polar aprotic solvent such as acetone, butanone, acetonitrile, N,N-dimethylformamide, N,N-dimethylacetamide or N-methylpyrrolidone. Also suitable for the preparation of the methyl ester is reaction with diazomethane in diethyl ether, tetrahydrofuran or tert.-butyl methyl ether.

The reaction is carried out at temperatures from 0° C. to the boiling point of the solvent used. A temperature range from 20° to 100° C. is preferred especially from 20° C. to 50° C.

Compounds of the general formula I in which $R^4$ is $(CH_2)_nCOR^8$ and $R^8$ is $C_1$-$C_4$-alkoxy or benzyloxy can also be obtained from other compounds of the same formula by transesterification (replacement of the alkoxy or benzyloxy radical by another alkoxy radical or by benzyloxy) by standard processes known to the expert. The solvent in which this reaction is preferably carried out is the alcohol which corresponds to the radical which is to be introduced; catalysts which can be used are either acids such as sulfuric acid, hydrochloric acid, p-toluenesulfonic acid, benzenesulfonic acid, camphorsulfonic acid, methanesulfonic acid or acidic ion exchanger resins, or bases such as potassium carbonate, sodium carbonate, the lithium, sodium, potassium or titanium alcoholate corresponding to the alcohol used as solvent, or titanium tetraisopropylate. Basic catalysts are preferred in this case.

The reaction is carried out at temperatures from 0° C. to the boiling point of the solvent used. A temperature range from 20° to 100° C. is preferred, especially from 50° to 80° C.

Compounds of the general formula I in which $R^4$ is $(CH_2)_nCOR^8$ and $R^8$ is NHOH, $NH_2$, $NHR^7$, $NR^7_2$, piperidino, pyrrolidino or morpholino can be prepared from compounds of the general formula I in which $R^4$ is $(CH_2)_nCOR^8$ and $R^8$ is OH by condensation with the appropriate amine $R^8H$ by processes known in principle to the expert. Examples of suitable condensing agents are carbonyldiimidazole, dicyclohexylcarbodiimide, diethoxyphosphonyl chloride, diethoxyphosphonyl azide, phosphorus oxychloride, propylphosphonic anhydride and diphenylphosphonyl chloride. The condensation is advanageously carried out in a solvent. Virtually all familiar organic solvents are suitable, depending on the condensing agent used, such as hydrocarbons (saturated or aromatic), chlorinated hydrocarbons, ethers, lower ketones such as acetone or butanone, tert.amides such as dimethylformamide, dimethylacetamide or N-methylpyrrolidone, lower alcohols such as methanol, ethanol, isoporpanol, n-, iso- or tert.butanol and even aqueous systems or mixtures (homogeneous or two-phase) of water with the organic solvents listed.

A preferred embodiment of this process comprises reacting the compounds of the general formula I in which $R^4$ is $(CH_2)_nCOR^8$ and $R^8$ is OH with carbonyldiimidazole in an aprotic solvent, especially tetrahydrofuran, at temperatures from 0° to 20° C., followed by addition of the amine component $R^8H$.

Alternatively, the carboxylic acid component can first be converted into an activated derivative (acid chloride, mixed anhydride) and the latter can then be reacted with the amine $R^8H$, preferably in the presence of an auxiliary base such as sodium bicarbonate, sodium carbonate, potassium carbonate, sodium hydroxide solution or potassium hydroxide solution, or a tertiary amine such as pyridine, lutidine or a trialkylamine such as triethylamine, diisopropylethylamine or tributylamine. The expert is familiar with a large number of methods for activating carboxylic acids, for example reaction with thionyl chloride, phosphorus trichloride, phosgene or oxalyl chloride to give the acid chloride, or reaction with chloroformic esters or sulfonyl chlorides (methanesulfonyl chloride, trifluoromethanesulfonyl chloride or benzenesulfonyl chloride) in the presence of bases, preferably of tert.amines such as triethylamine or pyridine, to give the mixed anhydrides.

A preferred embodiment of this process comprises reacting the compounds of the general formula I in which $R^4$ is $(CH_2)_nCOR^8$ and $R^8$ is OH with ethyl chloroformate in the presence of triethylamine in methylene chloride at temperatures from −20° to 5° C., followed by addition of the amine component $R^8H$. Compounds of the general formula I in which $R^4$ is $(CH_2)_nCOR^8$ and $R^8$ is NHOH, $NH_2$, $NHR^7$, $NR^7_2$, piperidino, pyrrolidino or morpholino can also be prepared from compounds of the general formula I in which $R^4$ is $(CH_2)_nCOR^8$ and $R^8$ is $C_1-C_4$-alkoxy, benzyloxy or phenoxy, by aminolysis with the appropriate amine $R^8H$. The reaction is preferably carried out in a suitable solvent such as an alcohol (methanol, ethanol, n-propanol, n-butanol, isopropanol, 2-ethoxyethanol or 2-methoxyethanol), an ether (preferably tetrahydrofuran, dioxane, 1,2-dimethoxyethane or diethylene glycol dimethyl ether) or a hydrocarbon such as toluene, xylene, mesitylene, tetralin or decalin. It is also possible to use an excess of the amine $R^8H$ as solvent. The reaction is carried out at temperatures in the range from 20° C. to the boiling point of the solvent used, and preferred temperatures are from 40° to 120° C., especially from 40° to 80° C.

It is advantageous, especially with the low-boiling amines, to carry out the reaction under a pressure of inert gas (20–50 bar of $N_2$ or argon) in an autoclave.

It may be advantageous in some cases, especially with the low-boiling amines and in the case of hydroxylamine, to use in place of the free amine a salt of the amine with an organic or inorganic acid, and to liberate the amine therefrom in the reaction mixture with an auxiliary base. Suitable salts are, in particular, the hydrochlorides, hydrobromides, hydrogen sulfates, sulfates or acetates; suitable auxiliary bases are alkali metal and alkaline earth metal carbonates and bicarbonates, such as sodium carbonate, sodium bicarbonate, potassium carbonate, potassium bicarbonate, or calcium carbonate, or alkali metal salts of organic acids such as sodium acetate or potassium acetate, or tertiary amines, especially trialkylamines such as triethylamine, diisopropylethylamine, tributylamine or trioctylamine. The reaction is preferably carried out in an alcohol, for example methanol, ethanol, n-propanol, n-butanol, isopropanol, 2-ethoxyethanol or 2-methoxyethanol as solvent, at temperatures from 20° to 120° C., especially from 40° to 100° C., possibly in an autoclave under a pressure of inert gas.

Compounds of the general formula I in which X is SO or $SO_2$ can be obtained from those compounds of the general formula I in which X is S by oxidation. Suitable oxidizing agents are, in particular, organic peracids such as 3-chloroperbenzoic acid, peracetic acid, perphthalic acid and perbenzoic acid. Aslo suitable are some inorganic oxidizing agents such as sodium periodate, potassium permanganate, sodium hydrochlorite, sodium chlorite and hydrogen peroxide.

The nature and amount of the oxidizing agent which is to be chosen depend on whether it is desired to oxidize to the stage of the sulfoxide or of the sulfone. Particularly suitable for selective oxidation to the sulfoxide are the organic peracids listed above (1 equivalent, reaction temperature −40° to 0° C. ) or sodium periodate; it is possible to use for the oxidation to the sulfone either an excess (2–3 equivalents) of organic peracid (reaction temperature 0° to 40° C.) or one of the listed inorganic oxidizing agents, with the exception of sodium periodate.

The reactions with peracids are preferably carried out in an organic solvent such as methylene chloride, methanol, ethanol, toluene or tetrahydrofuran, reaction with hydrogen peroxide is preferably carried out in acetic acid or acetic anhydride; suitable for the reaction with the other oxidizing agent are, especially, aqueous systems such as mixtures of methanol, acetone or acetic acid with water.

It may be advantageous in some of the processes described above the protect a reactive group which is present in the starting material, especially a hydroxyl group which is not intended to take part in the reaction, with a suitable protective group. Preferred protective groups are those, especially ethers or carbonates, which can be eliminated under mild acidic or neutral conditions or by hydrogenolysis, such as tert-butyl, benzyl, 4-methoxybenzyl, benzhydryl, methoxymethyl, 1-ethoxyethyl or tetrahydropyranyl ethers, silyl ethers such as trimethylsilyl or tert.-butyldimethylsilyl or carbonates such as benzyloxycarbonyl and tert.-butoxycarbonyl derivatives, which are well known from peptide and steroid chemistry.

After the main reaction has taken place, these protective groups can be removed in a generally known manner, for example by treatment with organic acids such as formic acid, acetic acid, trifluoroacetic acid or oxalic acid or a mixture thereof, optionally in the presence of water and/or inert organic solvents such as lower alcohols (for example methanol or ethanol) or cyclic ethers (for example tetrahydrofuran or dioxane) and with liberation of the hydroxyl. Suitable for eliminating silyl protective groups are fluorides such as KF, CsF or $Bu_4NF$. Suitable for eliminating benzyl, benzhydryl, 4-methoxybenzyl or benzyloxycarbonyl protective groups is also hydrogenation in the presence of a suitable catalyst, for example palladium, platinum, platinum oxide or nickel. This reaction is preferably carried out in an organic solvent, especially in a lower alcohol such as methanol or ethanol, or in acetic acid, possibly with the addition of water, under pressures of hydrogen from 1 to 200 bar, preferably from 1 to 100 bar, at temperatures from 20° to 100° C., preferably at 20° to 60° C., especially at room temperature (20°–30° C.).

The separation of the racemates produced in the synthesis of the compounds of the general formula I according to the invention into the two enantiomers, to which the invention likewise relates, is preferably carried out by chromatographic separation on an optically active support material. Examples of suitable materials are triacetylcellulose, tribenzoylcellulose or silica gel modified with dinitrobenzoylphenylglycine (so-called Perkle phases).

Also suitable for racemic resolution of the compounds of the general formula I, according to the invention, in which $R^3$ is OH is derivatization of this OH group with an optically active carboxylic acid (as ester) or an optically active isocyanate (as carbamate), followed by chromatographic separation of the resulting diastereomers and finally cleavage of the derivative again. Particularly suitable optically active aids are isocyanates such as dehydroabietyl isocyanate or (R)- or (S)-1-(1-naphthyl)ethyl isocyanate or N-protected natural amino acids such as (S)-N-methanesulfonylphenylalanine. The derivatization and the cleavage again are carried out by standard processes familiar to the expert.

Those compounds of the general formula I according to the invention which contain a carboxyl group can form salts with inorganic or organic bases. The present invention therefore also relates to such salts. Salts with inorganic bases are preferred, especially the physiologically acceptable alkali metal salts, in particular sodium and potassium salts.

The compounds of the general formula I according to the invention have valuable pharmacological properties; in particular, they antagonize the action of the leukotrienes.

The following experimental models were used to characterize the pharmacological properties.

The leukotriene-antagonistic action of the substances of the general formula I according to the invention is determined by the inhibition of the leukotriene-induced contraction of strips of guinea pig lung. The method which is used is a modification of the test described by Foreman, Shelly and Weber (Arch. Int. Pharmacodyn. 278, 193–206 (1985)).

Guinea pigs are sacrificed by an overdose of ether. The thoracic cavity is opened; the lungs are removed and cut into strips 5 cm long, which are stored in physiological saline. For the measurement, the strips of lung are placed in an organ bath filled with Ringer's solution which is equilibrated at 37° C. and through which carbogen ($O_2/CO_2$ 95:5 parts by volume) is passed. The strips are left to equilibrate under a load of 0.5–1 g for 30–60 minutes. The strips of lung are pretreated with indomethacin ($10^{-6}$ g/ml of bath liquid) before the test starts.

The contraction is induced by adding $LTC_4$, $LTD_4$ or $LTE_4$ in a concentration of 3 ng/ml of bath liquid. The test substances are administered therapeutically into the bath, after the maximum contraction plateau has been reached, in several concentrations and at time intervals of 10 minutes. 6–12 strips of lung are used for each concentration of the test substance.

The concentrations of the test substances at which the contraction is reduced by 50% ($IC_{50}$) are indicated in $\mu g/ml$.

The results of the pharmacological test on the following compounds are detailed hereinafter by way of example:

Compound A: Methyl (6RS)-7-(2-benzyloxyphenyl)-6-hydroxy-4-thiaheptanoate
Compound B: Methyl (6RS)-7-(2-benzyloxy-3-cyclopentylphenyl)-6-hydroxy-4-thiaheptanoate
Compound C: (6RS)-7-(2-Benzyloxy-3-cyclopentylphenyl)-6-hydroxy-4-thiaheptanoic acid
Compound D: Methyl (6RS)-7-(2-benzyloxy-5-chlorophenyl)-6-hydroxy-4-thiaheptanoate
Compound E: (5RS)-6-(2-benzyloxy-3-cyclopentylphenyl)-3-thiahexane-1,5-diol

| Compound | $IC_{50}$ [$\mu g/ml$] with respect to | | |
| --- | --- | --- | --- |
| | $LTC_4$ | $LTD_4$ | $LTE_4$ |
| A | 0.6–1.0 | 0.6 | 0.6–1.0 |
| B | 0.6 | 1.0 | 3.0 |
| C | 3.0–6.0 | 3.0–6.0 | 3.0 |
| D | 6.0–10 | 3.0 | 1.0–3.0 |
| E | 6.0–10 | 6.0–10 | 1.0–3.0 |

The compounds according to the invention are, by reason of their pharmacological properties, suitable for the treatment of allergic and inflammatory disorders such as asthma, allergic skin reactions, psoriasis, ulcerative colitis or rheumatoid arthritis, as well as shock.

Hence the invention also relates to the use of the compounds of the formula I according to the invention for the treatment and prophylaxis of the disorders listed above.

The invention furthermore embraces the use of the compounds according to the invention for the preparation of pharmaceuticals used for the treatment and prophylaxis of the abovementioned disorders.

The invention further relates to pharmaceuticals which contain one or more compounds of the general formula I according to the invention, and/or their pharmacologically tolerated salts.

The pharmaceuticals are prepared by processes known per se and familiar to the expert. The pharmacologically active compounds (=active substance) according to the invention are used as pharmaceuticals either as such or, preferably, in combination with suitable pharmaceutical auxiliaries in the form of tablets, coated tablets, capsules, suppositories, emulsions, suspensions, creams, ointments, granules, powders or solutions, with the content of active substance advantageously being between 0.1 and 95%.

The particular auxiliaries suitable for the desired pharmaceutical formulation are familiar to the expert on the basis of his expert knowledge. Apart from solvents, gelling agents, suppository bases, tablet auxiliaries and other active substance vehicles, it is possible to use, for example, antioxidants, dispersing agents, emulsifiers, antifoam agents, flavorings, preservatives, solubilizers or colorants.

The active substances can be administered topically, orally, parenterally, intravenously, rectally or by inhalation, with the preferred mode of administration being dependent on the disorder to be treated.

For a form for oral administration, the active compounds are mixed with the additives suitable for this purpose, such as excipients, stabilizers or inert diluents, and converted by the customary methods into suitable dosage forms such as tablets, coated tablets, hard gelatin capsules, aqueous, alcoholic or oily suspensions or aqueous, alcoholic or oily solutions. Examples of inert vehicles which can be used are gum arabic, magnesia, magnesium carbonate, potassium phosphate, lactose, glucose or starch, especially corn starch. In this connection, preparation can be effected both as dry and as wet granules. Examples of suitable oily excipients or solvents are vegetable or animal oils, such as sunflower oil or fish liver oil.

For subcutaneous or intravenous administration, the active compounds, or the physiologically tolerated salts thereof, are converted into a solution, suspension or emulsion, if desired with the substances customary for this purpose, such as solubilizers, emulsifiers or other auxiliaries. Examples of suitable solvents are water, physiological saline or alcohols, for example ethanol, propanol and glycerol, as well as sugar solutions such as glucose or mannitol solutions, or else a mixture of the various solvents mentioned.

Pharmaceutical products for topical and local use are, for example for treating the skin, lotions and creams which contain a liquid or semi-solid oil-in-water or water-in-oil emulsion, and ointments (which preferably contain a preservative). Suitable for treating the eyes are eyedrops which contain the active compound in aqueous or oily solution. Suitable for treatment of the nose are aerosols and sprays, similar to those described hereinafter for treating the airways, coarse powders which are administered by rapid inhalation through the nostrils, and in particular nose drops which contain the active compounds in aqueous or oily solution.

Examples of pharmaceutical formulations suitable for administration in the form of aerosols or sprays are solutions, suspensions or emulsions of the active substance of the general formula I according to the invention in a pharmaceutically acceptable solvent such as, especially, ethanol or water, or a mixture of such solvents. The formulation can, where required, also contain other pharmaceutical auxiliaries such as surfactants, emulsifiers and stabilizers, as well as a propellant gas. A formulation of this type normally contains the active substance in a concentration of about 0.1 to 10, in particular of about 0.3 to 3, % by weight.

The dosage of the active substance of the formula I which is to be administered, and the frequency of administration, depend on the strength of action and duration of action of the compound used; as well as on the nature and severity of the disorder which is to be treated and on the sex, age, weight and individual response of the mammal which is to be treated. On average, the recommended daily dose of a compound of the formula I according to the invention would probably be, for a mammal weighing about 75 kg—primarily a human—in the range from about 10 to 500 mg, preferably between about 25 and 250 mg, it being possible for administration to take place in several doses a day as required.

The examples which follow are intended to illustrate the present invention without, however, restricting its scope.

Rf values were determined on precoated silica gel plates (5×10 cm, layer thickness 0.25 mm, silica gel 60 $F_{256}$) from Riedel de Haen. The stated solvent ratios are ratios by volume. The following are stated for NMR spectra: measurement frequency in MHz, solvent, chemical shift for each signal in ppm (relative to tetramethylsilane as standard), multiplicity, any coupling constants in Hz, and number of protons from the integration. Multiplicities are specified by the following abbreviations: s=singlet, d=doublet, t=triplet, q=quartet, m=multiplet, AB=AB system; more complicated signals are indicated by combination of these letters, for example dt=doublet of triplets; broad signals are indicated by addition of "br".

Mass spectra were recorded either by electron-impact ionization, fast atom bombardment (FAB) or direct chemical ionization (DCI).

The progress of the reactions was generally followed by thin-layer chromatography; reaction times are therefore stated only by way of example. Solutions were concentrated using a rotary evaporator under a pressure of 1-200 torr and at bath temperatures of 20°-80° C., depending on the solvent.

Where no melting point is given, the relevant compound is a liquid.

EXAMPLE 1

Methyl 7-(2-benzyloxy-3-cyclopentylphenyl)-6-hydroxy-4-thiaheptanoate (a) 486.7 g (3.0 mol) of 2-cyclopentylphenol, 472 g (3.9 mol) of allyl bromide and 830 g (6.0 mol) of potassium carbonate are heated under reflux in 2.5 l of acetone while stirring vigorously for 26 h. The cooled reaction mixture is filtered, and the filtrate is concentrated in vacuo. The residue is taken up in petroleum ether, and the solution is washed three times with 2N sodium hydroxide solution. The organic phase is dried over magnesium sulfate and concentrated in vacuo, and the residue is finally distilled in vacuo. 593 g (97% of theory) of 2-cyclopentylphenyl allyl ether are obtained.

Boiling point 134° C./12 torr Rf=0.65 (cyclohexane/ethyl acetate 5:1)

$C_{14}H_{18}O$: Mass spectrum (MS) molar peak: m/e=202

$^1$H-NMR (60 MHz, CDCl$_3$, δ ppm): 1.4–2.2 (m, 8H), 3.35 (m, 1H), 4.25 (m, 2H), 5.0–5.35, 5.45, 5.7–6.4 (each m, Σ3H), 6.6–7.2 (m, 4H).

The following are prepared analogously:
4-Chlorophenyl allyl ether $C_9H_9ClO$ MS m/e=168
2,4-Dimethylphenyl allyl ether $C_{11}H_{14}O$ MS m/e=162

(b) 290 g (1.43 mol) of 2-cyclopentylphenyl allyl ether are heated under a nitrogen atmosphere at 220° C. for 4h. The crude product is purified by column chromatography on silica gel (mobile phase cyclohexane/ethyl acetate 50:1). Besides 20 g of 4-allyl-2-cyclopentylphenol there are obtained 203 g (70% of theory) of 2-allyl-6-cyclopentylphenol.

Rf=0.42 (0.19 for the p-isomer) cyclohexane/ethyl acetate 9:1

$C_{14}H_{18}O$ MS m/e=202

$^1$H-NMR (60 MHz, CDCl$_3$ δ ppm): 1.4–2.2 (m, 8H), 3.0–3.5 (m, 3H), 5.0, 5.2, 5.6–6.4 (each m, Σ3H), 6.6–7.2 (m, 3H).

The following were prepared analogously:
2-Allyl-4-chlorophenol $C_9H_9ClO$ Ms m/e=168
2-Allyl-4,6-dimethylphenol $C_{11}H_{14}O$ MS m/e=162

(c) 90 g (0.44 mol) of 2-allyl-6-cyclopentylphenol, 62 g (0.49 mol) of benzyl chloride and 124 g (0.9 mol) of potassium carbonate are heated under reflux in 800 ml of acetone for 70 h. The cooled reaction mixture is filtered, and the filtrate is concentrated. The residue is taken up in petroleum ether, and the solution is washed three times with 2N sodium hydroxide solution and then once each with water and saturated brine. The organic phase is dried over sodium sulfate and concentrated in vacuo. The residue is distilled in vacuo. 118 g (92% of theory) of 1-allyl-2-benzyloxy-3-cyclopentylbenzene are obtained.

Boiling point 165°–170° C./0.1–0.5 torr $C_{21}H_{24}O$ MS m/e=292

Rf=0.58 (mobile phase cyclohexane/ethyl acetate 9:1)

$^1$H-NMR (60 MHz, CDCl$_3$, δ ppm): 1.4–2.2 (m, 8H), 3.4 (m,3H//4.75 (s, 2H), 4.83, 5.1, 5.6–6.2 (each m, Σ3H), 6.8–7.4 (m, 8H).

The following were prepared analogously:
1-Allyl-2-benzyloxybenzene $C_{16}H_{16}O$ MS m/e=224
1-Allyl-2-benzyloxy-5-chlorobenzene $C_{16}H_{15}ClO$ MS m/e=258
1-Allyl-2-benzyloxy-3,5-dimethylbenzene $C_{18}H_{20}O$ MS m/e=252
1-Allyl-2-benzyloxy-3-methylbenzene $C_{17}H_{18}O$ MS m/e=238
1-Allyl-2-(3-methoxybenzyl)-3-cyclopentylbenzene $C_{22}H_{26}O_2$ Ms m/e=322
1-Allyl-2-(2-methoxybenzyl)-3-cyclopentylbenzene $C_{22}H_{26}O_2$ MS m/e=322
1-Allyl-2-(4-methoxybenzyl)-3-cyclopentylbenzene $C_{22}H_{26}O_2$ MS m/e=322
1-Allyl-2-[3-(4-acetyl-3-hydroxy-2-propylphenoxy)-propyloxy]-3-cyclopentylbenzene $C_{32}H_{44}O_7S$ MS m/e=572

(d) 20 g (0.0684 mol) of 1-allyl-2-benzyloxy-3-cyclopentylbenzene are dissolved in 200 ml of dichloromethane. While stirring and cooling in an ice bath, 14 g (0.081 mol) of m-chloroperbenzoic acid are added in portions. The mixture is allowed to reach room temperature and, after 2.5 h, a further 5 g of m-chloroperbenzoic acid are added. The mixture is further stirred at room temperature overnight, and then the precipitated m-chlorobenzoic acid is removed by filtration and the filtrate is concentrated in vacuo. The oily residue is thoroughly stirred with n-pentane and filtered, and the filtrate is washed three times with 2N sodium hydroxide solution and then once with saturated brine. Drying over sodium sulfate is followed by removal of the solvent by distillation in vacuo. 23.9 g of (2-benzyloxy-3-cyclopentylbenzyl)oxirane are obtained as an oil.

$C_{21}H_{24}O_2$ MS m/e=308

$^1$H-NMR (60 MHz, CDCl$_3$, δ ppm): 1.4–2.2 (m, 8H), 2.2–3.8 (m, Σ4H), 4.8 (s, 2H), 7.0–7.6 (m, 8H).

The following were prepared analogously:

(2-Benzyloxybenzyl)oxirane $C_{16}H_{16}O_2$ MS m/e=240

(2-Benzyloxy-5-chlorobenzyl)oxirane $C_{16}H_{15}ClO_2$ MS m/e=274

(2-Benzyloxy-3,5-dimethylbenzyl)oxirane $C_{18}H_{20}O_2$ MS m/e=268

(2-Benzyloxy-3-methylbenzyl)oxirane $C_{17}H_{18}O_2$ MS m/e=254

[3-Cyclopentyl-2-(3-methoxybenzyloxy)benzyl]oxirane $C_{22}H_{26}O_3$ MS m/e=338

[3-Cyclopentyl-2-(2-methoxybenzyloxy)benzyl]oxirane $C_{22}H_{26}O_3$ MS m/e=338

[3-Cyclopentyl-2-(4-methoxybenzyloxy)benzyl]oxirane $C_{22}H_{26}O_3$ MS m/e=338

{2-[3-(4-Acetyl-3-hydroxy-2-propylphenoxy)-propyloxy]-3-cyclopentylbenzyl}oxirane $C_{32}H_{44}O_8S$ MS m/e=588

(e) 20 g (59 mmol) of (2-benzyloxy-3-cyclopentylbenzyl)-oxirane, 24.5 g (0.204 mol) of methyl-3-mercaptopropionate and 26.1 g (0.257 mol) of triethylamine are stirred in 150 ml of dry methanol at room temperature and under protective gas (argon or nitrogen) overnight. The solvent is removed by distillation in vacuo, and the residue is chromatographed on a silica gel column (gradient dichloromethane→ethyl acetate). 19.0 g (65% of theory) or methyl 7-(2-benzyloxy-3-cyclopentylphenyl)-6-hydroxy-4-thiaheptanoate are obtained.

Rf=0.34 (cyclohexane/ethyl acetate 2:1)

$C_{25}H_{32}O_4S$ MS m/e=428

$^1$H-NMR (270 MHz, CDCl$_3$, δ ppm): 1.5–1.9 and 2.1 (m, Σ8H), 2.55 (t, 2H), 2.65 (m, 2H), 2.79 (m, 2H), 2.90 (dd, 2H), 3.41 (m, 1H), 3.68 (s, 3H), 4.00 (m, 1H), 4.87 (s, 2H), 7.09, 7.20, 7.3–7.5 (each m, Σ8H).

The following compounds were prepared in analogy to Example 1:

EXAMPLE 2

Methyl 7-(2-benzyloxy-5-chlorophenyl)-6-hydroxy-4-thiaheptanoate $C_{20}H_{23}ClO_4S$ MS m/e=394

$^1$H-NMR (60 MHz, CDCl$_3$, δ in ppm): 2.6–3.0 (m, 9H), 3.72 (s, 3H), 3.8–4.2 (m, 1H), 5.07 (s, 2H), 6.6–7.2 (m, 3H), 7.40 (s, 5H).

EXAMPLE 3

Methyl 7-(2-benzyloxy-3,5-dimethylphenyl)-6-hydroxy-4-thiaheptanoate $C_{22}H_{28}O_4S$ MS m/e=388

Rf=0.23 (cyclohexane/ethyl acetate 4:1)

$^1$H-NMR (60 MHz, CDCl$_3$, δ in ppm): 2.30 (s, 6H), 2.4–3.0 (m, 9H), 3.70 (s, 3H), 4.0 (m, 1H), 4.85 (s, 2H), 6.93 (s br, 2H), 7.44 (s br, 5H).

EXAMPLE 4

Methyl 7-(2-benzyloxy-3-methylphenyl)-6-hydroxy-4-thiaheptanoate $C_{21}H_{26}O_4S$ MS m/e=374

Rf=0.21 (cyclohexane/ethyl acetate 4:1)

$^1$H-NMR (60 MHz, CDCl$_3$, δ in ppm): 2.35 (s, 3H), 2.4–3.0 (m, 9H), 3.70 (s, 3H), 4.0 (m, 1H), 4.87 (s, 2H), 7.10 (s br, 3H), 7.45 (s br, 5H).

EXAMPLE 5

Methyl 7-(2-benzyloxyphenyl)-6-hydroxy-4-thiaheptanoate $C_{20}H_{24}O_4S$ MS m/e=360

Rf=0.20 (cyclohexane/ethyl acetate 4:1)

$^1$H-NMR (60 MHz, CDCl$_3$, δ in ppm): 2.4–3.0 (m, 9H), 3.70 (s, 3H), 3.8–4.2 (m, 1H), 5.12 (s, 2H), 6.8–7.5 (m)+7.43 (s br) Σ9H.

EXAMPLE 6

Methyl 7-[3-cyclopentyl-2-(3-methoxybenzyloxy)phenyl]-6-hydroxy-4-thiaheptanoate $C_{26}H_{34}O_5S$ MS m/e=458

Rf=0.15 (cyclohexane/ethyl acetate 4:1)

$^1$H-NMR (60 MHz, CDCl$_3$, δ in ppm): 1.3–2.2 (m, 8H), 2.4–3.0 (m, 9H), 3.3–3.6 (m, 1H), 3.70 (s, 3H), 3.87 (s, 3H), 3.8–4.2 (m, 1H), 4.86 (s, 2H), 6.8–7.5 (m, 7H).

EXAMPLE 7

Methyl 7-[3-cyclopentyl-2-(2-methoxybenzyloxy)phenyl]-6-hydroxy-4-thiaheptanoate $C_{26}H_{34}O_5S$ MS m/e=458

Rf=0.14 (cyclohexane/ethyl acetate 4:1)

$^1$H-NMR (60 MHz, CDCl$_3$, δ in ppm): 1.3–2.2 (m, 8H), 2.4–3.0 (m, 9H), 3.3–3.6 (m, 1H), 3.70 (s, 3H), 3.87 (s, 3H), 3.8–4.2 (m, 1H), 4.86 (s, 2H), 6.8–7.6 (m, 7H).

EXAMPLE 8

Methyl 7-[3-cyclopentyl-2-(4-methoxybenzyloxy)phenyl]-6-hydroxy-4-thiaheptanoate $C_{26}H_{34}O_5S$ MS m/e=458

Rf=0.12 (cyclohexane/ethyl acetate 4:1)

$^1$H-NMR (60 MHz, CDCl$_3$, δ in ppm): 1.3–2.2 (m, 8H), 2.4–3.0 (m, 9H), 3.3–3.6 (m, 1H), 3.70 (s, 3H), 3.86 (s, 3H), 3.8–4.2 (m, 1H), 4.80 (s, 2H), 6.97 (d, 8–9 Hz)+6.8–7.5 (m)+7.43 (d, 8–9 Hz) Σ7H.

EXAMPLE 9

Methyl 6-(2-benzyloxy-3-cyclopentylphenyl)-5-hydroxy-3-thiahexanoate $C_{24}H_{30}O_4S$ MS m/e=414

Rf=0.18 (cyclohexane/ethyl acetate 4:1)

$^1$H-NMR (60 MHz, CDCl$_3$, δ in ppm): 1.3–2.2 (m, 8H), 2.5–3.1 (m, 5H), 3.25 (s, 2H), 3.3–3.6 (m, 1H), 3.70 (s, 3H), 3.8–4.2 (m, 1H), 4.86 (s, 2H), 7.0–7.3 (m, 3H), 7.43 (s br, 5H).

EXAMPLE 10

6-(2-Benzyloxy-3-cyclopentylphenyl)-3-thiahexane-1,5-diol $C_{23}H_{30}O_3S$ MS m/e=386

$^1$H-NMR (60 MHz, CDCl$_3$, δ in ppm):
1.2–2.2 (m, 8H), 2.5–3.0 (m, 6–7H), 3.70 (t, 6 Hz, 2H), 4.03 (quintuplet br, 5–6 Hz, 1H), 4.88 (s, 2H), 7.0–7.3 (m, 3H), 7.45 (s br, 5H).

EXAMPLE 11

7-(2-Benzyloxy-3-cyclopentylphenyl)-4-thiaheptane-1,2,6-triol $C_{24}H_{32}O_4S$ MS m/e=416

$^1$H-NMR (270 MHz, CDCl$_3$, δ in ppm): 1.5–1.75 (m, 4H), 1.75–1.9 (m, 2H), 2.0–2.1 (m, 2H), 2.5–2.6 (m, 2H), 2.65–2.75 (m, 2H) 2.87 (m, 2H), 3.417 (quintuplet, 9 Hz, 1H), 3.492 (dd, 11 Hz, 7 Hz, 1H), 3.6–3.8 (m, 2H), 4.03 (m, 1H), 5.866 (s, 2H), 7.052 (dd, 7–8 Hz, 3 Hz, 1H), 7.104 (t, 7–8 Hz, 1H), 7.242 (dd, 7–8 Hz, 3 Hz, 1H), 7.3–7.5 (m, 5H).

EXAMPLE 12

Methyl 7-{2-[3-(4-acetyl-3-hydroxy-2-propylphenoxy)-propyloxy]-3-cyclopentylphenyl}-6-hydroxy-4-thiaheptanoate $C_{32}H_{44}O_7S$ MS m/e=572

$^1$H-NMR (270 MHz, CDCl$_3$, δ in ppm): 0.925 (t, 8 Hz, 3H), 1.45–1.6 (m, 8), 1.7–1.8 (m, 2H), 1.9–2.05 (m, 2H), 2.326 (quintuplet, 6 Hz, 2H), 2.478 (dd, 14 Hz, 8 Hz, 1H); 2.581 (s, 3H), 2.55–2.7 (m, 6H), 2.75–2.85 (m, 4H), 3.259 (quintuplet, 8–9 Hz, 1H), 3.693 (s, 3H), 3.9–4.1 (m, 3H), 4.326 (t, 6 Hz, 2H), 6.518 (d, 8 Hz, 1H), 7.0–7.1 (m, 2H), 7.13–7.2 (m, 1H), 7.625 (d, 8 Hz, 1H), 12.75 (s, 1H).

EXAMPLE 13

Methyl 6-[3-cyclopentyl-2-(3-methoxybenzyloxy)phenyl]-5-hydroxy-3-thiahexanoate $C_{25}H_{32}O_5S$ MS m/e=444

$^1$H-NMR (60 MHz, CDCl$_3$, δ in ppm): 1.3–2.2 (m, 8H), 2.4–3.1 (m, 5H), 3.26 (s, 2H), 3.3–3.6 (m, 1H), 3.70 (s, 3H), 3.87 (s, 3H), 3.8–4.2 (m, 1H), 4.86 (s, 2H), 6.8–7.5 (m, 7H).

EXAMPLE 14

7-(2-Benzyloxy-3-cyclopentylphenyl)-6-hydroxy-4-thiaheptanoic acid 0.675 g (1.63 mmol) of methyl 7-(2-benzyloxy-3-cyclopentylphenyl)-6-hydroxy-4-thiaheptanoate (Example 1) is dissolved in 10 ml of methanol/water 9:1, and 0.7 g (17.5 mmol) of NaOH dissolved in a little water is added. The mixture is left to stir at room temperature overnight, then the solvent is removed by distillation in vacuo, and the residue is acidified with cold 1N hydrochloric acid. Three extractions with diethyl ether are carried out, and the organic phases are washed twice with saturated brine and dried over sodium sulfate, and the solvent is removed by distillation in vacuo. 444 mg (66% of theory) of 7-(2-benzyloxy-3-cyclopentylphenyl)-6-hydroxy-4-thiaheptanoic acid are obtained.

Rf=0.46 (mobile phase chloroform/methanol 4:1)

$C_{24}H_{30}O_4S$ MS m/e=414

$^1$H-NMR (60 MHz, CDCl$_3$, δ ppm): 1.5–2.2 (m), 2.4–3.0 (m), 3.50 (m, 1H), 4.00 (m, 1H), 4.85 (s, 2H), 7.0–7.6 (m, 8H).

The following were prepared in analogy to Example 14:

EXAMPLE 15

7-(2-Benzyloxy-5-chlorophenyl)-6-hydroxy-4-thiaheptanoic acid $C_{19}H_{21}ClO_4S$ MS m/e=380

$^1$H-NMR (60 MHz, CDCl$_3$, δ in ppm): 2.6–3.0 (m, 9H), 3.8–4.2 (m, 1H), 4.99 (s, 2H), 6.6–7.2 (m, 4H), 7.32 (s, 5H).

EXAMPLE 16

7-(2-Benzyloxy-3,5-dimethylphenyl)-6-hydroxy-4-thiaheptanoic acid $C_{21}H_{26}O_4S$ MS m/e=374

EXAMPLE 17

7-(2-Benzyloxy-3-methylphenyl)-6-hydroxy-4-thiaheptanoic acid $C_{20}H_{24}O_4S$ MS m/e=360

EXAMPLE 18

7-[3-Cyclopentyl-2-(3-methoxybenzyloxy)phenyl]-6-hydroxy-4-thiaheptanoic acid $C_{25}H_{32}O_5S$ MS m/e=444

EXAMPLE 19

6-(2-Benzyloxy-3-cyclopentylphenyl)-5-hydroxy-3-thiahexanoic acid $C_{23}H_{28}O_4S$ MS m/e=400

EXAMPLE 20

6-[3-Cyclopentyl-2-(3-methoxybenzyloxy)phenyl]-5-hydroxy-3-thiahexanoic acid $C_{24}H_{30}O_5S$ MS m/e=430

EXAMPLE 21

Sodium 7-(2-benzyloxy-3-cyclopentylphenyl)-6-hydroxy-4-thiaheptanoate

Variant 1:

100 mg of 7-(2-benzyloxy-3-cyclopentylphenyl)-6-hydroxy-4-thiaheptanoic acid (Example 10) are dissolved in 5 ml of methanol, and 10 mg of sodium hydroxide in 0.5 ml of water are added. The mixture is left to stir at room temperature for 1 h and then the solvent is removed by evaporation in vacuo. Toluene is added to the residue and is evaporated off in vacuo (repeated twice). The residue is dried at the oil pump. 100 mg of the product are obtained.

Rf=0.35 (chloroform/methanol 5:1)

Variant 2:

0.1 g of methyl 7-(2-benzyloxy-3-cyclopentylphenyl)-6-hydroxy-4-thiaheptanoate (Example 1) is dissolved in a little methanol/water 9:1, and 1.1 equivalents of 2N sodium hydroxide solution are added. The mixture is left to stir at room temperature overnight, and then the solvent is removed by distillation in vacuo, and further working up is carried out as described in under Variant 1. 85 mg of the product are obtained.

Rf=0.35 (chloroform/methanol 5:1)

EXAMPLE 22

Methyl (+)-7-(2-benzyloxy-3-cyclopentylphenyl)-6-hydroxy-4-thiaheptanoate and

EXAMPLE 23

Methyl (−)-7-(2-benzyloxy-3-cyclopentylphenyl)-6-hydroxy-4-thiaheptanoate

Racemic methyl 7-(2-benzyloxy-3-cyclopentylphenyl)-6-hydroxy-4-thiaheptanoate (Example 1) is separated into the enantiomers by HPLC on acetyl cellulose (mobile phase ethanol). The spectroscopic data are identical to those of the racemate.

EXAMPLE 24

7-(2-Benzyloxy-3-cyclopentylphenyl)-6-hydroxy-4-thiaheptane-1,6-diol 1 g (2.33 mmol) of methyl 7-(2-benzyloxy-3-cyclopentylphenyl)-6-hydroxy-4-thiaheptanoate (Example 1) is dissolved in 3 ml of tetrahydrofuran, and the solution is added dropwise to 250 mg of lithium aluminum hydride in 20 ml of tetrahydrofuran. The mixture is left to stir at room temperature for 30 min and then, with caution, 0.25 ml of water, 0.25 ml of 15% strength sodium hydroxide solution and 0.73 ml of water are successively added. The precipitate is filtered off, the filtrate is washed once with saturated brine and dried over magnesium sulfate, and the solvent is removed by distillation in vacuo. The residue is purified by chromatography on silica gel (mobile phase cyclohexane/ethyl acetate 1:1). 745 mg of 7-(2-benzyloxy-3-cyclopentylphenyl)-6-hydroxy-4-thiaheptane-1,6-diol are obtained.

$C_{24}H_{32}O_3S$ MS m/e=400

$^1$H-NMR (60 MHz, CDCl$_3$, δ ppm): 1.4–2.2 (m, 10–11H), 2.4–3.0 (m, 6–7H), 3.2–4.2 (m)+3.71 (t, 6 Hz) Σ4H), 4.90 (s, 2H), 7.0–7.3 (m, 3H), 7.45 (s br, 5H).

EXAMPLE 25

Ethyl 7-(2-benzyloxy-3-cyclopentylphenyl)-6-hydroxy-4-thiaheptanoate 1 g (2.33 mmol) of methyl 7-(2-benzyloxy-3-cyclopentylphenyl)-6-hydroxy-4-thiaheptanoate (Example 1) is dissolved in 5 ml of ethanol, and 2.5 g of potassium carbonate are added. The mixture is left to stir with exclusion of moisture overnight and is filtered, and the filtrate is evaporated in vacuo. The residue is taken up in ether, and the solution is washed with water and saturated brine. Drying over sodium sulfate and evaporation in vacuo result in 0.51 g of ethyl 7-(2-benzyloxy-3-cyclopentylphenyl)-6-hydroxy-4-thiaheptanoate.

Rf=0.38 (mobile phase cyclohexane/ethyl acetate 2:1)

$C_{26}H_{34}O_4S$ MS m/e=442

$^1$H-NMR (60 MHz, CDCl$_3$, δ ppm): 1.25 (t, 3H), 1.4–2.2 (m, 8H), 2.4–3.0 (m, 8–9H, 4.15 (q, 2H), 4.86 (s, 2H), 7.0–7.3 (m, 3H), 7.45 (s br, 5H).

EXAMPLE 26

Isopropyl 7-(2-benzyloxy-3-cyclopentylphenyl)-6-hydroxy-4-thiaheptanoate 1 g (2.33 mmol) of methyl 7-(2-benzyloxy-3-cyclopentylphenyl)-6-hydroxy-4-thiaheptanoate (Example 1) is dissolved in 10 ml of isopropanol, and 0.36 ml (1.2 mmol) of titanium (IV) isopropylate is added. The reaction mixture is boiled with exclusion of moisture for 6 h and, after cooling, is poured into 100 ml of 2N hydrochloric acid, and the mixture is extracted three times with n-pentane. Drying over sodium sulfate, evaporation in vacuo and chromatography on silica gel (mobile phase cyclohexane/ethyl acetate 3:1) result in 0.8 g of isopropyl 7-(2-benzyloxy-3-cyclopentylphenyl)-6-hydroxy-4-thiaheptanoate.

Rf=0.39 (mobile phase cyclohexane/ethyl acetate 2:1)

$C_{27}H_{36}O_4S$ MS m/e=456

$^1$H-NMR (60 MHz, CDCl$_3$, δ ppm): 1.25 (d, 6H), 1.4–2.2 (m, 8H), 2.4–3.0 (m, 9H), 3.1–3.6 (m, 1H), 3.8–4.2 (m, 1H), 4.90 (s, 2H), 5.03 (quintuplet, 6 Hz, 1H), 7.0–7.3 (m, 3H), 7.45 (s br, 5H).

EXAMPLE 27

4-[5-(2-Benzyloxy-3-cyclopentylphenyl)-4-hydroxy-2-thiapentyl]-1,3-dioxolan-2-one 200 mg (0.48 mmol) of 7-(2-benzyloxy-3-cyclopentylphenyl)-4-thiaheptane-1,2,6-triol (Example 11) are dissolved in 3 ml of tetrahydrofuran, and 150 mg (0.93 mmol) of N,N'-carbonyldiimidazole are added. The solution is stirred at 70° C. with exclusion of moisture for 5 h and then diluted with ether and washed once with 1N sodium hydroxide solution and twice with saturated brine. Drying over sodium sulfate, removal of the solvent by distillation in vacuo and chromatography on silica gel (mobile phase cyclohexane/ethyl acetate 1:1) yields 133 mg of 4-[5-(2-benzyloxy-3-cyclopentylphenyl)-4-hydroxy-2-thiapentyl]-1,3-dioxolan-2-one.

Rf=0.34 (mobile phase cyclohexane/ethyl acetate 1:1)

$C_{25}H_{30}O_5S$ MS m/e=442

$^1$H-NMR (60 MHz, CDCl$_3$, δ ppm): 1.5–2.1 (m), 2.5–3.0 (m), 3.40 (m, 1H), 4.00 (m, 1H), 4.20 (m, 1H), 4.48 (m, 1H), 4.75 (m, 1H), 4.88 (s, 2H), 7.0–7.5 (m, 8H).

EXAMPLE 28

Methyl 7-(3-cyclopentyl-2-hydroxyphenyl)-6-hydroxy-4-thiaheptanoate

This compound is obtained in analogy to Example 1e from (3-cyclopentyl-2-hydroxybenzyl)oxirane (prepared from Example 1b in analogy to Example 1d) and methyl 3-mercaptopropionate.

$C_{18}H_{26}O_4S$ MS m/e=308

$^1$H-NMR (270 MHz, CDCl$_3$, δ in ppm): 1.5–1.9 (m, 6H), 2.0–2.1 (m, 2H), 2.488 (dd, 15 Hz, 11 Hz, 1H), 2.614 (t, 7 Hz, 2H), 2.75–2.9 (m, 4H), 2.974 (dd, 15 Hz, 3 Hz, 1H), 3.389 (quintuplet, 8–9 Hz, 1H), 3.718 (s, 3H), 3.98–4.08 (m, 1H), 6.802 (t, 8 Hz, 1H), 6.873 (dd, 8 Hz, 3 Hz, 1H), 7.137 (dd, 8 Hz, 3 Hz, 1H).

EXAMPLE 29

Sodium 7-(3-cyclopentyl-2-hydroxyphenyl)-6-hydroxy-4-thiaheptanoate

Prepared from Example 28 by hydrolysis in analogy to Example 21.

$C_{17}H_{24}O_4S$ MS m/e=294

EXAMPLE 30

7-(2-Benzyloxy-3-cyclopentylphenyl)-6-hydroxy-4-thiaheptanohydroxamic acid 0.65 g of NaOH is dissolved in 3 ml of water and 10 ml of methanol. 0.57 g of hydroxylamine hydrochloride is added, and then, while stirring, 1 g of methyl 7-(2-benzyloxy-3-cyclopentylphenyl)-6-hydroxy-4-thiaheptanoate (Example 1) dissolved in 10 ml of methanol is added. After the mixture has been stirred at room temperature for one hour it is diluted with 50 ml of water and extracted 3x with ethyl acetate, and the extracts are washed with water and saturated brine, dried over $MgSO_4$ and concentrated in vacuo. The residue is purified by chromatography on silica gel (mobile phase ethyl acetate/toluene/pyridine 49:49:2). 0.5 g of a viscous oil is obtained.

Rf=0.2 (ethyl acetate)
$C_{24}H_{31}NO_4S$ MS (FAB) m/e=430 (M+H$^+$)
$^1$H-NMR (60 MHz, CDCl$_3$, δ ppm): 1.3–2.2 (m, 8H), 2.2–3.0 (m, 11H), 3.2–3.7 (m, 1H), 3.8–4.2 (m, 1H), 4.88 (s, 2H), 7.0–7.3 (m, 3H), 7.45 (s br, 5H), The following are obtained in analogy to Example 30:

EXAMPLE 31

6-(2-Benzyloxy-3-cyclopentylphenyl)-5-hydroxy-3-thiahexanohydroxamic acid

Rf=0.1 (ethyl acetate/methanol/acetic acid 95:5:1)
$C_{23}H_{29}NO_4S$ MS (DCI) m/e=416 (M+H$^+$)
$^1$H-NMR (60 MHz, CDCl$_3$, δ ppm): 1.3–2.2 (m, 8H), 2.2–3.0 (m, 7H), 3.2 (s br, 2H), 3.2–3.7 (m, 1H), 3.8–4.2 (m, 1H), 4.87 (s, 2H), 6.9–7.3 (m, 3H), 7.45 (s br, 5H)

EXAMPLE 32

7-[2-(4-Methoxybenzyloxy)-3-cyclopentylphenyl]-6-hydroxy-4-thiaheptanohydroxamic acid Rf=0.23 (ethyl acetate/acetic acid 98:1)
$C_{25}H_{33}NO_5S$ MS (DCI) m/e=416 (M+H$^+$)
$^1$H-NMR (60 MHz, CDCl$_3$, δ ppm): 1.3–2.2 (m, 8H), 2.4–3.0 (m, 11H), 3.3–3.6 (m, 1H), 3.83 (s, 3H), 3.8–4.2 (m, 1H), 4.80 (s, 2H), 6.97 (d, 8–9 Hz) + 6.8–7.5 (m)+7.43 (d, 8–9 Hz) Σ7H.

EXAMPLE 33

Methyl 7-(2-benzyloxy-3-cyclopentylphenyl)-6-hydroxy-4-oxo-4-thiaheptanoate 1 g of methyl 7-(2-benzyloxy-3-cyclopentylphenyl)-6-hydroxy-4-thiaheptanoate (Example 1) is dissolved in 10 ml of THF. While stirring and cooling in an ice bath, 0.47 g of 3-chloroperbenzoic acid (technical 85% pure) is introduced in portions. The mixture is then left to stir at room temperature for 90 min and is diluted with ethyl acetate, washed with 2N sodium hydroxide solution (2x) and saturated brine, dried over $MgSO_4$ and concentrated in vacuo. The crude product is purified by column chromatography on silica gel (toluene/ethyl acetate 4:1→2:1). 0.95 g of a viscous oil is obtained.

Rf=0.07 (toluene/ethyl acetate 1:1)
$C_{25}H_{32}O_5S$ MS (DCI) m/e=445 (M+H$^+$)
$^1$H-NMR (60 MHz, CDCl$_3$, δ ppm): 1.5–2.3 (m, 8H), 2.6–3.1 (m, 9H), 3.2–3.6 (m, 1H), 3.72 (s, 3H), 4.3–4.7 (m, 1H), 4.87 (s, 2H), 7.0–7.4 (m, 3H), 7.45 (s br, 5H)

EXAMPLE 34

Methyl 7-(2-benzyloxy-3-cyclopentylphenyl)-6-hydroxy-4,4-dioxo-4-thiaheptanoate 1 g of methyl 7-(2-benzyloxy-3-cyclopentylphenyl)-6-hydroxy-4-thiaheptanoate (Example 1) is dissolved in 10 ml of THF. While stirring and cooling in an ice bath, 0.95 g of 3-chloroperbenzoic acid (technical 85% pure) is introduced in portions. The mixture is then left to stir at room temperature to 90 min and is diluted with ethyl acetate, washed with 2N sodium hydroxide solution (2x) and saturated brine, dried over $MgSO_4$ and concentrated in vacuo. The crude product is purified by column chromatography on silica gel (toluene/ethyl acetate 4:1→2:1). 0.90 g of a viscous oil is obtained.

Rf=0.22 (toluene/ethyl acetate 1:1)
$C_{25}H_{32}O_5S$ MS (DCI) m/e=460
$^1$H-NMR (60 MHz, CDCl$_3$, δ ppm): 1.5–2.3 (m, 8H), 2.6–3.1 (m, 5H), 3.15–3.6 (m, 5H), 3.72 (s, 3H), 4.3–4.7 (m, 1H), 4.88 (s, 2H), 7.0–7.4 (m, 3H), 7.45 (s br, 5H).

EXAMPLE 35

7-(2-Benzyloxy-3-cyclopentylphenyl)-6-hydroxy-4-thiaheptanamide 1 g of methyl 7-(2-benzyloxy-3-cyclopentylphenyl)-6-hydroxy-4-thiaheptanoate (Example 1) is dissolved in 20 ml of an approximately 10% strength solution of ammonia in methanol, and the solution is left to stand in a closed vessel at room temperature for 7 days. The solvent is removed by distillation in vacuo, and the residue is purified by column chromatography on silica gel (mobile phase ethyl acetate/cyclohexane 1:4).

$C_{24}H_{31}NO_3S$ MS m/e=413
$^1$H-NMR (60 MHz, CDCl$_3$, δ ppm): 1.4–2.3 (m, 8H), 2.4–3.0 (m, 9H), 3.2–3.6 (m, 1H), 4.03 (m, 1H), 4.87 (s, 2H), 4.3–5.8 (m, 2H), 7.0–7.4 (m, 3H), 7.45 (s br, 5H).

EXAMPLE 36

Methyl 6-{2-[3-(4-acetyl-3-hydroxy-2-propylphenoxy)-propyloxy]-3-cyclopentylphenyl}-5-hydroxy-3-thiahexanoate is prepared in analogy to Example 1.
$C_{31}H_{42}O_7S$ MS m/e=558
$^1$H-NMR (270 MHz, CDCl$_3$, δ in ppm): 0.917 (t, 8 Hz, 3H), 1.45–1.6 (m, 8), 1.7–1.8 (m, 2H), 1.9–2.05 (m, 2H), 2.326 (quintuplet, 6 Hz, 2H), 2.585 (s, 3H), 2.5–2.75 (m, 4H), 2.84 (d, 7 Hz, 2H), 3.268 (s, 2H), 3.15–3.3 (m, 1H), 3.703 (s, 3H), 3.9–4.1 (m, 3H), 4.321 (t, 6 Hz, 2H), 6.527 (d, 9 Hz, 1H), 7.0–7.1 (m, 2H), 7.13–7.2 (m, 1H), 7.622 (d, 9 Hz, 1H), 12.75 (s, 1H).

EXAMPLE 37

Methyl 7-(3-cyclopentyl-2-propargyloxyphenyl)-6-hydroxy-4-thiaheptanoate is prepared in analogy to Example 1.
$C_{21}H_{28}O_4S$ MS m/e=376
$^1$H-NMR (60 MHz, CDCl$_3$, δ in ppm): 1.3–2.35 (m, 8H), 2.57 (t, 2.5 Hz), 2.5–2.9 (m), 3.0 (s) Σ10H, 3.2–3.6 (m, 1H), 3.71 (s, 3H), 4.04 (quintet br., 6 Hz, 1H), 4.55 (d, 2.5 Hz, 2H), 7.0–7.5 (m, 3H)

EXAMPLE 38

Methyl 7-[3-cyclopentyl-2-(oct-2-yn-1-yloxy)phenyl]-6-hydroxy-4-thiaheptanoate is prepared in analogy to Example 1.

$C_{26}H_{38}O_4S$ MS m/e=446

$^1$H-NMR (60 MHz, CDCl$_3$, δ in ppm): 0.90 ("t" br, 4–5 Hz, 3H), 1.1–2.5 (m, 16H), 2.5–3.0 (m), 3.0 (s) Σ9H, 3.2–3.6 (m, 1H), 3.71 (s, 3H), 4.04 (quintet br., 6 Hz, 1H), 4.52 (t, 2 Hz, 2H), 7.0–7.5 (m, 3H).

We claim:

1. A compound of the formula I:

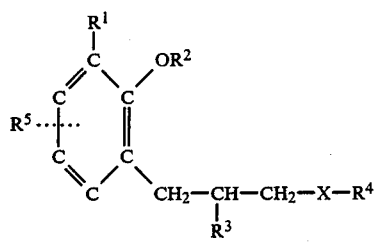

wherein the radicals have the following meaning:
X is O, S, SO OR SO$_2$;
R$^1$ is H, straiqht-chain or branched C$_1$–C$_{12}$-alkyl, C$_2$–C$_{12}$-alkenyl or C$_2$–C$_{12}$-alkynyl, or is C$_3$–C$_8$-cycloalkyl, C$_3$–C$_8$-cycloalkenyl, halogen, phenoxy, CF$_3$, NO$_2$, OH, OR$^6$, COOH, COOR$^6$, CHO or COR$^7$;
R$^2$ is H, straight-chain or branched C$_1$–C$_{12}$-alkyl, C$_2$–C$_{12}$-alkenyl or C$_2$–C$_{12}$-alkynyl, or is C$_3$–C$_8$-cycloalkyl, C$_3$–C$_8$-cycloalkenyl, phenyl-C$_1$–C$_{10}$-alkyl, phenoxy-C$_1$–C$_{10}$-alkyl, phenyl-C$_2$–C$_{10}$-alkenyl or phenyl-C$_2$–C$_{10}$-alkynyl, it being possible for the phenyl rings also to be substituted by 1–3 C$_1$–C$_4$-alkyl, C$_2$–C$_4$-alkenyl, C$_1$–C$_4$-alkoxy, C$_1$–C$_4$-alkanoyl, C$_1$–C$_4$-alkoxycarbonyl, hydroxyl or halogen radicals;
R$^3$ is OH, OR$^6$ or OCOR$^7$;
R$^4$ is a group of the formula (CH$_2$)$_n$COR$^8$;
R$^5$ is H, halogen, CF$_3$, OH, C$_1$–C$_4$-alkyl or C$_1$–C$_4$-alkoxy;
R$^6$ is C$_1$–C$_4$-alkyl, allyl or benzyl;
R$^7$ is C$_1$–C$_4$-alkyl or phenyl;
R$^8$ is OH, C$_1$–C$_4$-alkoxy, OCH$_2$CO$_2$H, OCH$_2$CO$_2$R$^7$, OCH$_2$Ph, NHOH, NH$_2$, NHR$^7$, NR$^7{}_2$, phenoxy or phenoxy substituted by carboxyl, C$_1$–C$_4$-alkoxycarbonyl, OH or OCH$_3$; and
n is 0, 1, 2 or 3;
as well as pharmaceutically acceptable salts of a compound of the formula I in which one of the radicals contains a carboxyl group.

2. A compound as claimed in claim 1 and of the formula I, in which the radicals have the following meaning:
X is O, S, SO or SO$_2$;
R$^1$ is H, C$_1$–C$_4$-alkyl, C$_3$–C$_8$-cycloalkyl or C$_3$–C$_8$-cycloalkenyl;
R$^2$ is H, straight-chain or branched C$_1$–C$_{10}$-alkyl, C$_3$–C$_8$-cycloalkyl, phenyl-C$_1$–C$_{10}$-alkyl or phenoxy-C$_1$–C$_{10}$-alkyl, it being possible for the phenyl rings also to be substituted by 1–3 C$_1$–C$_4$-alkyl, C$_2$–C$_4$-alkenyl, C$_1$–C$_4$-alkoxy, C$_1$–C$_4$-alkanoyl, C$_1$–C$_4$-alkoxycarbonyl, hydroxyl or halogen radicals;
R$^3$ is OH;
R$^4$ is a group of the formula (CH$_2$)$_n$COR$^8$;
R$^5$ is H or halogen;
R$^7$ is C$_1$–C$_4$-alkyl;
R$^8$ is OH, C$_1$–C$_4$-alkoxy, OCH$_2$CO$_2$H, OCH$_2$CO$_2$R$^7$, OCH$_2$Ph, NHOH, NH$_2$, NHR$^7$, NR$^7{}_2$, phenoxy or phenoxy substituted by carboxy, C$_1$–C$_4$-alkoxycarbonyl, OH or OCH$_3$; and
n is 1, 2 or 3.

3. A compound as claimed in claim 1 and of the formula I, in which the radicals have the following meaning:
X is S;
R$^1$ is H, CH$_3$ or cyclopentyl;
R$^2$ is H, benzyl or benzyl substituted once or twice on the phenyl ring by methoxy or chlorine, is phenoxy-C$_2$–C$_4$-alkyl, it being possible for the phenyl ring also to be substituted by 1–3 C$_1$–C$_4$-alkyl, C$_1$–C$_4$-alkanoyl or hydroxy groups;
R$^3$ is OH;
R$^4$ is a group of the formula (CH$_2$)$_n$COR$^8$;
R$^5$ is H or chlorine;
R$^7$ is C$_1$–C$_4$-alkyl;
R$_8$ is OH, C$_1$–C$_4$-alkoxy, OCH$_2$CO$_2$H, OCH$_2$CO$_2$R$^7$, OCH$_2$Ph, NHOH, NH$_2$, phenoxy or phenoxy substituted by carboxyl, C$_1$–C$_4$-alkoxycarbonyl, OH or OCH$_3$; and
n is 1, 2 or 3.

4. Methyl (6RS)-7-(2-benzyloxyphenyl)-6-hydroxy-4-thiaheptanoate.

5. Methyl (6RS)-7-(2-benzyloxy-3-cyclopentylphenyl)-6-hydroxy-4-thiaheptanoate.

6. Methyl (6RS)-7-(2-benzyloxy-3-methylphenyl)-6-hydroxy-4-thiaheptanoate.

7. Methyl (6RS)-7-(2-benzyloxy-3,5-dimethylphenyl)-6-hydroxy-4-thiaheptanoate.

8. (6RS)-7-(2-Benzyloxy-3-cyclopentylphenyl)-6-hydroxy-4-thiaheptanoic acid.

9. Methyl (6RS)-7-(2-benzyloxy-5-chlorophenyl)-6-hydroxy-4-thiaheptanoate.

10. A pharmaceutical composition comprising an amount effective for use in the therapy of a mammal of a compound of the formula I according to claim 1 or of a physiologically tolerated salt of a compound of the formula I in which one of the radicals contains a carboxyl group, together with a pharmaceutically acceptable carrier.

11. A method for the treatment of a mammal suffering from a disorder associated with elevated levels of leukotrienes which comprises administering to said mammal an amount effective for said treatment of a pharmaceutical composition according to claim 10.

12. The method of claim 11 for the treatment of a mammal suffering from asthma.

13. A method for the treatment of a mammal suffering from a disorder associated with elevated levels of leukotrienes which comprises administering to said mammal an amount effective for said treatment of a compound of the formula I according to claim 1 or of a physiologically tolerated salt of a compound of the formula I in which one of the radicals contains a carboxyl group.

14. The method of claim 13 for the treatment of a mammal suffering from asthma.

* * * * *